United States Patent [19]

Koe

[11] 4,320,124

[45] Mar. 16, 1982

[54] COMPOSITION FOR ENHANCING BINDING OF A BENZODIAZEPINE TO CENTRAL BENZODIAZEPINE RECEPTORS AND USE THEREOF

[75] Inventor: Billie K. Koe, Gales Ferry, Conn.

[73] Assignee: Pfizer Inc., New York, N.Y.

[21] Appl. No.: 197,872

[22] Filed: Oct. 17, 1980

[51] Int. Cl.³ ..................... A61K 31/33; A61K 31/47
[52] U.S. Cl. .................................. 424/244; 424/258
[58] Field of Search ................. 424/258, 244; 546/108

[56] References Cited

U.S. PATENT DOCUMENTS 3,862,986  1/1975  Hellerback ........................ 424/258

OTHER PUBLICATIONS

Derwent Abst., Japan Pat. 002491 (30-10-72).

*Primary Examiner*—Stanley J. Friedman
*Attorney, Agent, or Firm*—Charles J. Knuth; Albert E. Frost; Peter C. Richardson

[57] ABSTRACT

Pharmaceutical compositions comprising the combination of a benzodiazepine and certain 1,9-dihydroxyoctahydrophenanthridine and 1-hydroxyhexahydrophenanthridine-9(8H)-one analgesic agents to enhance the binding of said benzodiazepine to central benzodiazepine receptors, and a method for the use thereof.

15 Claims, No Drawings

COMPOSITION FOR ENHANCING BINDING OF A BENZODIAZEPINE TO CENTRAL BENZODIAZEPINE RECEPTORS AND USE THEREOF

BACKGROUND OF THE INVENTION

This invention relates to compositions comprising a benzodiazepine and certain analgesic agents which enhance the binding of said benzodiazepine to central benzodiazepine receptors. More particularly it is concerned with compositions of the foregoing type which achieve a potentiation of said benzodiazepine receptor binding in mammals, including man, to which they are administered.

The benzodiazepines, a unique class of anxiolytic, anticonvulsant and sedative-hypnotic drugs, are the most widely prescribed "minor tranquilizers" in use today. When administered via the oral route, they become widely distributed throughout the body, particularly in lipid-rich tissues such as adipose and brain. The publication "Sleeping Pills, Insomnia and Medical Practice, Report of a Study of the Institute of Medicine", National Academy of Sciences, Washington D.C., 1979, reports that pharmacologically active metabolites of the benzodiazepines are frequently long-lived. The impairment in "next-day" functioning when benzodiazepines are used as hypnotics is considered attributable to the delay in excretion of said metabolites. Still further, cumulative dose effects have been disclosed in the above-cited report following long-term use of benzodiazepines. Other problems associated with use of benzodiazepines are physical withdrawal symptoms after abrupt cessation of moderate to high doses and interaction with other central nervous system (CNS) depressants, especially alcohol.

Enhancement of benzodiazepine binding in vitro and enhancement of the pharmacological effects of diazepam in vivo by $N^6$-[2-(4-chlorophenyl)]-bicyclo-[2.2.2]-octyl-(3)-adenosine (EMD 28422) has been reported by Skolnick et al., Pharmacol. Biochem. & Behavior, 12, 685–689 (1980). Williams et al., European J. Pharmacol. 56, 273–276 (1979) found that Avermectin $B_{1a}$, a macrocyclic lactone disaccharide anthelmintic agent, enhance the in vitro binding of diazepam to rat and mouse brain membranes.

Other substances such as divalent nickel ions, gamma-aminobutyric acid and 5-aminomethyl-3-hydroxyisoxazole have also been reported to enhance in vitro binding of diazepam.

It is, therefore, apparent that development of a formulation and/or method which permits use of smaller doses of a benzodiazepine but which achieves at least the same level of effectiveness thereof is highly desirable.

SUMMARY OF THE INVENTION

It has now been found that compositions comprising a benzodiazepine and certain analgesic agents effectively enhance the binding of said benzodiazepine to benzodiazepine receptors in the brain of a mammal to which said composition is administered.

The use of the term "a benzodiazepine" is meant to include not only the 1,4-benzodiazepines, but also the 1,4-benzodiazepine-2-ones and the 4-oxides thereof; the 1,5-benzodiazepines; and 2,4-benzodiazepines; the triazolo-1,4-benzodiazepines; and heterodiazepines such as 4,3-e-pyrazolodiazepines; and pharmaceutically acceptable salts of said compounds; and others described by Sternbach in "Progress in Drug Research", Vol. 22, Edited by E. Jucker (1978), Birkhauser Verlag, Basel, pp. 229–266.

The enhancement of benzodiazepine binding to benzadiazepine receptors is observed with phenanthridine type analgesic agents of formula I:

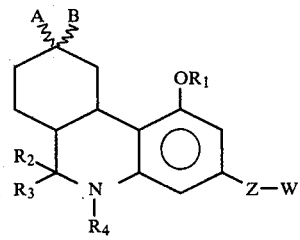

wherein
A and B when taken together are oxo;
A when taken individually is hydrogen;
B when taken individually is hydroxy or alkanoyloxy having from two to five carbon atoms;
$R_1$ is hydrogen or alkanoyl having from two to five carbon atoms;
$R_2$ is hydrogen or $(C_{1-6})$alkyl;
$R_3$ is hydrogen, methyl or ethyl;
$R_4$ is hydrogen, alkanoyl having from two to five carbon atoms or $(C_{1-6})$alkyl;
Z is alkylene having from one to nine carbon atoms or -(alk$_1$)$_m$-O-(alk$_2$)$_n$- wherein each of (alk$_1$) and (alk$_2$) is alkylene having from one to nine carbon atoms, with the proviso that the summation of carbon atoms in (alk$_1$) plus (alk$_2$) is not greater than nine; each of m and n is 0 or 1; and
W is hydrogen, pyridyl or

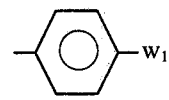

wherein $W_1$ is hydrogen, fluoro or chloro.

Also useful in this invention are pharmaceutically acceptable acid addition salts of compounds of formula I. Representative of such salts are mineral acid salts such as the hydrochloride, hydrobromide, sulfate, nitrate, phosphate; organic acid salts such as the citrate, acetate, sulfosalicylate, tartrate, glycolate, malonate, maleate, fumarate, malate, 2-hydroxy-3-naphthoate, pamoate, salicylate, stearate, phthalate, succinate, gluconate, mandelate, lactate and methane sulfonate.

DETAILED DESCRIPTION OF THE INVENTION

The compounds of formula I are prepared according to procedures described in Belgian Pat. No. 854,655.

Compounds having the formula I contain asymmetric centers at the 6a- and/or 10a-positions. There may be additional asymmetric centers in the 3-position substituent (-Z-W), and 5-, 6- and 9-positions. Diastereomers with the 9-beta-configuration are generally favored over the 9-alpha-isomers because of greater (quantitatively) biological activity. For the same reason, the trans(6a,10a)diastereomers of compounds of formula I are generally favored over the cis (6a,10a)-diastereomers. As regards compounds of formula I wherein A and B taken together are oxo, when one of $R_2$ and $R_3$ is other than hydrogen, the cis-diastereomers are preferred because of their greater biological activity. Among the enantiomers of a given compound, one will generally be favored over the other and the racemate because of its greater activity. The enantiomer favored is determined by the procedures described herein. For example, the l-enantiomer of 5,6,6a-beta, 7,8,9,10,10a-alpha-octahydro-1-acetoxy-9-beta-hydroxy-6-beta-methyl-3-(5-phenyl-2-pentyloxy)phenanthridine is favored over the d-enantiomer and the racemate because of its greater enhancement of binding of a benzodiazepine to central benzodiazepine receptors.

Among the 3-position (ZW) diastereoisomers, one will generally be favored over the other. For example, dl-5,6,6a-beta,7,8,9-alpha,10,10a-alpha-octahydro-1-acetoxy-9-hydroxy-6-beta-methyl-3-(1-alpha-methyl-4-phenylbutoxy)phenanthridine is favored over dl-5,6,6a-beta,7,8,9-alpha, 10,10a-alpha-octahydro-1-acetoxy-9-hydroxy-6-beta-methyl-3-(1-beta-methyl-4-phenylbutoxy)phenanthridine and (2'R,6S,6aR,9R,10aR)-(−)-1-acetoxy-5,6,6a,7,8,9,10,10a-octahydro-9-hydroxy-6-methyl-3-(5'-phenyl-2'-pentyloxy)phenanthridine is favored over (2'S,6S,6aR,9R,10aR)-(−)-1-acetoxy-5,6,6a,7,8,9,10,10a-octahydro-9-hydroxy-6-methyl-3-(5'-phenyl-2'-pentyloxy)phenanthridine because of their greater enhancement of binding. For convenience, the above formula is considered to be generic to and embracive of the racemic modifications of the compounds of this invention, the diastereomeric mixtures, the pure enantiomers and diastereomers thereof. The utility of the racemic mixtures, the diastereomeric mixtures as well as of the pure enantiomers and diastereomers is determined by the biological evaluations described below.

The l-enantiomers of formula I compounds appear to be stereospecifically adapted for enhancing benzodiazepine binding. The sterospecificity is supported by the absence of enhancement of benzodiazepine binding by the d-enantiomers. For this reason the l-enantiomers are the favored forms of formula I compounds, even over the racemates.

Favored, because of their greater effectiveness relative to that of other compounds of formula I are those wherein $R_1$ is hydrogen or alkanoyl;
$R_3$ is hydrogen, methyl or ethyl; and each of $R_2$ and $R_4$ is hydrogen or alkyl;
Z and W have the values shown below:

| Z | m | n | W |
|---|---|---|---|
| alkylene having from 5 to 9 carbon atoms | — | — | H |
| alkylene having from 2 to 5 carbon atoms | — | — | $C_6H_5$, 4-$FC_6H_4$, 4-$ClC_6H_4$, 4-pyridyl |
| —(alk$_1$)$_m$—O—(alk$_2$)$_n$— | 1 | 1 | $C_6H_5$, 4-$FC_6H_4$, 4-$ClC_6H_4$, 4-pyridyl |
| | 0 | 1 | |
| | 1 | 1 | |
| —(alk$_1$)$_m$—O—(alk$_2$)$_n$— | 1 | 1 | H |
| | 0 | 1 | H |
| | 1 | 0 | H |

Preferred compounds are those favored compounds described above wherein B represents hydroxy, A is hydrogen and which have the trans-configuration, especially those wherein:
A is hydrogen;

B is hydroxy;
$R_1$ is hydrogen or acetyl;
$R_3$ is hydrogen;
$R_2$ is methyl or propyl;
$R_4$ is hydrogen, methyl or ethyl;
Z is alkylene having from 2 to 5 carbon atoms when W is phenyl or pyridyl;
when Z is -(alk$_1$)$_m$-O-(alk$_2$)$_n$- wherein m is 0 and n is 1, (alk$_2$)$_n$ is alkylene having from four to nine carbon atoms, W is hydrogen or phenyl; and
when Z is alkylene having from five to nine carbon atoms, W is hydrogen.

Especially preferred are those preferred compounds wherein $R_1$ is acetyl; $R_3$ is hydrogen, $R_2$ is $\beta$-methyl; $R_4$ is hydrogen or methyl; and Z-W is 5-phenyl-2-pentyloxy.

The favored benzodiazepines are the 1,4-benzodiazepines including 7-chloro-2-methylamino-5-phenyl-3H-1,4-benzodiazepine-4-oxide (chlordiazepoxide); 8-chloro-6-phenyl-4H-[1,2,4]-triazolo[4,3-a][1,4]-benzodiazepine; 7-chloro-1,3-dihydro-3-hydroxy-5-phenyl-2H-1,4-benzodiazepin-2-one; 10-chloro-11b-(2-chlorophenyl)-2,3,7,11b-tetrahydrooxazolo[3,2-d][1,4]benzodiazepin-6(5H)-one; 8-chloro-6-(2-chlorophenyl)-4H-[1,2,4]-(3-chlorotriazolo)[4,3-a][1,4]-benzodiazepine; 7-chloro-1,3-dihydro-1-methyl-5-phenyl-2H-1,4-benzodiazepine; 7-chloro-1,3-dihydro-1-methyl-5-(cyclohex-1-enyl)-2H-1,4-benzodiazepin-2-one; 7-bromo-1,3-dihydro-5-(2-pyridyl)-2H-1,4-benzodiazepin-2-one; and those having formula II:

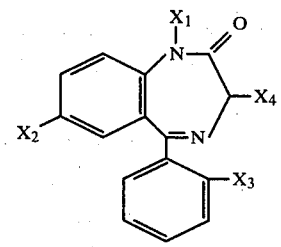

II wherein the variables have the following values:

| | $X_1$ | $X_2$ | $X_3$ | $X_4$ |
|---|---|---|---|---|
| (a) | $CH_3$ | Cl | H | H (diazepam) |
| (b) | H | Cl | H | OH |
| (c) | H | Cl | H | H |
| (d) | $CH_3$ | $NO_2$ | F | H (flunitrazepam) |
| (e) | $CH_2CH\equiv CH$ | Cl | H | H |
| (f) | $CH_3$ | $NO_2$ | H | H |
| (g) | $CH_2CH_2N(C_2H_5)_2$ | Cl | F | H |
| (h) | H | Cl | H | COOK . KOH |
| (i) | H | $NO_2$ | Cl | H |
| (j) | H | Cl | Cl | OH |
| (k) | $CH_2-\triangleleft$ | Cl | H | H |
| (l) | H | $NO_2$ | H | H |
| (m) | $CH_3$ | Cl | H | OH |
| (n) | $CH_3$ | Cl | H | $OCON(CH_3)_2$ |

The preferred benzodiazepines are chlorodiazepoxide and those of formula II tabulated above, especially compounds (a), (b), (d) and (g).

The benzodiazepines described herein are known compounds and are prepared by procedures described in the art.

In general, the amount of analgesic agent to be used for enhancing the binding of the benzodiazepine to central benzodiazepine receptors can vary over a wide range. However, in practice it is advantageous, if only from an economical standpoint, to use a semi-equal amount by weight of the benzodiazepine compound and even an equal amount or excess thereof as it is the cheaper of the two components. Optimum results are obtained with from about one to about 100 parts by weight of the benzodiazepine compound to about one part by weight of the analgesic agent of formula I. Thus, weight ratios of analgesic agent of formula I to benzodiazepine of from 1:1 to 1:100 can be used to enhance binding of the benzodiazepine and, hence, its anxiolytic effect.

The enhanced binding of the benzodiazepine compound to benzodiazepine receptors realized by the compositions of this invention make it possible to use less of the benzodiazepine component than would normally be used to achieve a given effect, e.g., anxiolytic.

The advantages afforded by use of compositions of this invention are self-evident in the light of the undesirable effects cited above.

The benzodiazepine and analgesic agent compounds can be administered concurrently as a single dosage composition or formulation. Alternatively, they can be administered concurrently as separate dosage forms. Still further, the analgesic agent can be administered either before or after administration of the benzodiazepine provided the time interval between the two is not too lengthy; i.e., not more than one hour. When given separately, the analgesic and benzodiazepine can be given by the same or different routes of administration. It is, however, for convenience to the patient and physician, preferred to use the two components; i.e., analgesic agent and benzodiazepine, as a single composition; i.e., a mixture, via a single route of administration.

A preferred unit dosage form for administering these novel compositions is most conveniently a powdered mixture of the two principal components encased in a soft or hard-shelled gelatin capsule. This dosage form may contain from about 1.0 mg up to about 100 mg of the desired benzodiazepine together with from about 0.01 to about 5 parts by weight of the chosen analgesic agent. An inert diluent, such as a pharmaceutically-acceptable inert carrier like starch, lactose or milk sugar, or glucosamine, may also be present if so desired. Conversely, it is also possible to administer these compositions in a granulated form as such or else compressed into tablets for oral administration, as well as in the form of aqueous suspensions, elixirs, lozenges, troches, hard candies and pediatric drops, etc. When administered parenterally, they can be given to the mammal in the form of an aqueous dispersion or solution for intravenous injection, or as an organic solution or suspension for intramuscular injection.

The method (or process) of this invention, and compositions for accomplishing said method, can be conducted with the use of more than one benzodiazepine, or with more than one form thereof, such as the base form and a salt thereof. Further, the analgesic agent can be used in more than one form, e.g., as the alcohol (formula I, B=OH, $R_1$=OH) or as an ester (formula I, B=OH, $R_1$=OCOCH$_3$), or more than one analgesic agent can be used. However, in actual practice, only one benzodiazepine and one analgesic agent are used, and only one form of each component.

The physician will determine the dosage which will be most suitable for an individual patient depending upon the age, weight and response of the particular patient and the rate of administration. Generally, however, the initial dose of a composition of this invention is administered in an amount to provide from about 4.0 to about 100 mg/day of benzodiazepine and from about 0.01 to about 5 mg/day of analgesic agent, in single or divided doses.

The ability of a given analgesic agent of formula I to enhance the binding of a benzodiazepine to central benzodiazepine receptors is determined by the following procedures.

Enhancement of $^3$H-Diazepam Binding to Rat Cortical Membranes (Benzodiazepine Receptors) in vitro by Nantradol[a] and Levonantradol[b]

Brains were removed from Sprague-Dawley CD male rats (Charles River Breeding Laboratories, Inc., Wilmington, MA; 200–250 g) following decapitation. The cortex was rapidly dissected and homogenized in 100 volumes (w/v) of ice-cold 50 mM Tris.HCl* buffer pH 7.4 using a motorized homogenizer. The homogenate was centrifuged at 20,000×g for 10 minutes, and the pellet was dispersed in 100 volumes of fresh buffer and repelleted by centrigation. Final suspension of the pellet was made in 10 volumes of the buffer. Binding experiments were conducted by incubating triplicate mixtures of 0.1 ml of the membrane preparation, 0.02 ml of levonantradol or nantradol dissolved in ethanol to achieve a final concentration of $10^{-4}$M, and 1.0 ml of $^3$H-diazepam (76.8 Ci/mmole, New England Nuclear) at various final concentrations for 30 minutes at 0°–5° C. Cold 50 mM Tris.HCl pH 7.4 buffer (5 ml) was added to the triplicate set of incubation tubes, and the contents of each tube was filtered through Whatman GF/B glass fiber filters (2.4 cm diameter, 0.73 mm thickness, 1.0 μm retention efficiency, 5.5 ml/sec flow rate, 275 ml/mm water absorption) under vacuum. The tube was rinsed with 5 ml of buffer, and the wash fluid was passed through the same filter. Each filter was placed in a glass scintillation counting vial, and 10 ml of Aquasol-2 (liquid scintillation fluid available from New England Nuclear) were added. Vials were kept overnight and counted for radioactivity in a liquid scintillation counter. Nonspecific binding was determined by incubating triplicate mixtures containing $10^{-6}$M diazepam for each concentration of $^3$H-diazepam used. Specific binding was defined as the difference between total binding and binding in the presence of $10^{-6}$M diazepam.

Nantradol added to the incubation tubes at 100 μM was found to enhance the binding of $^3$H-diazepam to rat cortical membranes for ligand concentrations ranging from 0.32–10.0 nM (Table 1). Likewise, levonantradol at 100 μM was found to increase the binding of $^3$H-diazepam at ligand concentrations of 0.32–17.8 nM (Table 2).

Tris.HCl* = tris(hydroxymethyl)amino methane hydrochloride.

(a) Nantradol = racemate of compound of formula I wherein A, $R_2$ and $R_4$ are hydrogen; $R_1$ is acetyl; $R_3$ is β-methyl; B is β-hydroxy; Z-W is OCH(CH$_3$)(CH$_2$)$_3$C$_6$H$_5$. (±)-5,6,6aβ,7,8,9α,10,-10aα-octahydro-6β-methyl-3-(1-methyl-4-phenylbutoxy)-1,9-phenanthridinediol 1-acetate, hydrochloride.

(b) Levonantradol - a levo form of nantradol; (2) (−)-(6S,6aR,9R,10aR)-5,6,6a,7,8,9,10,10a-octahydro-6-methyl-3-[(R)-1-methyl-4-phenylbutoxy]-1,9-phenanthridinediol 1-acetate, hydrochloride.

TABLE 1

Enhancement of ³H-diazepam binding to rat cortical membranes by nantradol

| ³H-Diazepam Concentration nM | Specific Binding | | Percent Increase % |
|---|---|---|---|
| | Nantradol 100 μM | Control | |
| | cpm | | |
| 0.32 | 6975 | 5626 | 24 |
| 1.0 | 19204 | 15267 | 26 |
| 1.78 | 28742 | 24770 | 16 |
| 3.2 | 42392 | 35153 | 21 |
| 5.62 | 55470 | 45035 | 23 |
| 10.0 | 64005 | 59767 | 7 | cpm = counts per minute

TABLE 2

Enhancement of ³H-diazepam binding to rat cortical membranes by levonantradol

| ³H-Diazepam Concentration nM | Specific Binding | | Percent Increase % |
|---|---|---|---|
| | Levonantradol 100 μM | Control | |
| | cpm | | |
| 0.32 | 4936 | 3727 | 32 |
| 0.56 | 8282 | 6118 | 35 |
| 1.0 | 11568 | 9147 | 27 |
| 1.78 | 19291 | 16435 | 17 |
| 3.2 | 30747 | 25214 | 22 |
| 5.62 | 40721 | 29195 | 40 |
| 10.0 | 48923 | 40607 | 21 |
| 17.8 | 54836 | 49861 | 10 |

Increased Binding of ³H-Diazepam to Cortical Membranes of Rats Treated with Nantradol (enhanced binding ex vivo)

Rats in groups of 3 received nantradol, 32 μmoles/kg (15 mg/kg) or vehicle (ethanol-Emulphor EL-620* - saline/5:5:90) one hour before decapitation. Brains were rapidly removed, and the cortex was dissected. Pooled tissue of each treatment group was homogenized in 25 volumes (w/v) of 0.32 M sucrose, using a motor-driven pestle. The homogenate was centrifuged at 1000×g for 10 minutes, and the supernate was centrifuged at 17,000×g for 10 minutes. The pellet (P₂) was dispersed in 10 volumes of 50 mM Tris.HCl pH 7.4 buffer using a Brinkmann Polytron. Binding experiments with the two membrane preparations were conducted as described above for the in vitro studies.

*(Emulphor EL-620=a polyoxyethylated vegetable oil of specific gravity 1.04–1.05 available from Anlara Chemicals, New York, N.Y.)

³H-Diazepam binding to cortical membranes from nantradol-treated rats was greater than that to cortical membranes of control rats for each ligand concentration tested (0.32–17.8 mM) (Table 3).

TABLE 3

Increased binding of ³H-diazepam to cortical membranes of rats treated with nantradol

| H-diazepam Concentration nM | Specific Binding | | Percent Increase % |
|---|---|---|---|
| | Nantradol 32 μmoles/kg (15 mg/kg) | control | |
| | cpm | | |
| 0.32 | 2243 | 1577 | 42 |
| 1.0 | 5472 | 4259 | 29 |
| 1.78 | 8372 | 6713 | 25 |
| 3.2 | 14189 | 12213 | 16 |

TABLE 3-continued

Increased binding of ³H-diazepam to cortical membranes of rats treated with nantradol

| H-diazepam Concentration nM | Specific Binding | | Percent Increase % |
|---|---|---|---|
| | Nantradol 32 μmoles/kg (15 mg/kg) | control | |
| | cpm | | |
| 5.62 | 17927 | 15360 | 17 |
| 10.0 | 21822 | 15951 | 37 |
| 17.8 | 25100 | 18132 | 38 |

Increased Binding of ³H-Diazepam to Brain Membranes of Mice Treated with Levonantradol (enhanced binding ex vivo)

Mice (male Swiss albino, Charles River Breeding Laboratories, Inc., Wilmington, MA, 23–25 g) in groups of 3 received levonantradol, 1.0 μmole/kg (0.47 mg/kg) or vehicle (ethanol-Emulphor El-620-saline/5:5:90) s.c. 1 hour before sacrifice by cerevical dislocation. Brains were rapidly removed, pooled and homogenized in 25 volumes (w/v) of 50 mM Tris.HCl pH 7.4 buffer using a motorized homogenizer. The homogenate was centrifuged at 1000×g for 10 minutes, and the supernate was centrifuged at 17,000×g for 10 minutes. The pellet was dispersed in 10 volumes of the buffer. Binding experiments were conducted as described above for the in vitro studies.

³H-diazepam binding to whole brain membranes from levonantradol-treated mice was greater than that to corresponding membranes from control mice for each ligand concentration tested (0.32–17.8 nM) (Table 4).

TABLE 4

Increased binding of ³H-diazepam to whole brain membranes of mice treated with levonantradol

| ³H-Diazepam Concentration nM | Specific Binding | | Percent Increase % |
|---|---|---|---|
| | Levonantradol 1.0 μmole/kg (0.47 mg/kg) | Control | |
| | cpm | | |
| 0.32 | 2343 | 1890 | 24 |
| 0.56 | 3721 | 3207 | 16 |
| 1.0 | 6112 | 4844 | 26 |
| 1.78 | 9404 | 7672 | 23 |
| 3.2 | 12302 | 9804 | 26 |
| 5.62 | 16229 | 12996 | 25 |
| 10.0 | 19170 | 16665 | 15 |
| 17.8 | 20168 | 17974 | 12 |

Repetition of the above procedure but using N-methyllevonantradol in place of levonantradol produces similar results.

Enhancement of ³H-Flunitrazepam Binding to Mouse Brain in vivo by Levonantradol

In vivo effects of levonantradol and its (+)-enantiomer on ³H-flunitrazepam binding on mice were measured by the method of Chang and Snyder (Eur. J. Pharmacol., 48:213–218, 1978). Groups of 5 mice were treated subcutaneously with levonantradol or (+)-nantradol one hour prior to an intravenous injection of 200 μCi/kg tritiated flunitrazepam (86.4 Ci/mmole, New England Nuclear). Groups of 5 mice were treated with the drug vehicle (ethanol-Emulphor EL-620-saline/5:5:90) and run simultaneously as controls. Twenty minutes after the ³H-flunitrazepam injection, the mice were sacrificed by cervical dislocation, and the brains were removed and immediately frozen. Each brain was weighed quickly and homogenized in 40 volumes (w/v) of ice-cold 50 mM Tris.HCl pH 7.7 buffer, using a motorized homogenizer. Triplicate 1.0 ml samples were filtered through Whatman GF/B glass fiber filters under vacuum and washed with two 5 ml aliquots of the ice-cold buffer. The bound $^3$H-flunitrazepam was measured by adding the filters to vials containing 10 ml of Aquasol-2 (New England Nuclear Corp.) and counting the radioactivity by liquid scintillation spectroscopy. Bound $^3$H-flunitrazepam for drug-treated mice was calculated as percent of bound $^3$H-flunitrazepam for control mice.

Levonantradol was found to enhance the binding of $^3$H-flunitrazepam to mouse brain (Table 5) at doses as low as 0.32 μmoles/kg (0.15 mg/kg). In contrast, the (+)-enantiomer showed no enhancement of binding at doses up to 32 μmoles/kg (15 mg/kg) (Table 6). These results showed that the enhancement of $^3$H-flunitrazepam binding to benzodiazepine receptors in vivo is a stereospecific effect for levonantradol. This facilitation of binding to benzodiazepine receptors in vivo indicates that levonantradol potentiates the pharmacological effects of diazepam and other benzodiazepines.

TABLE 5

Enhancement of $^3$H-flunitrazepam binding to mouse brain in vivo by levonantradol

| Treatment | Dose s.c. μmoles/kg (mg/kg) | $^3$H-flunitrazepam binding % Control ± S.E. | No. of mice | Comparison with control |
|---|---|---|---|---|
| Control (vehicle) | — | 100 ± 4 | (10) | |
| Levonantradol | 3.2(1.5) | 122 ± 6 | (5) | P <.01 |
| Levonantradol | 1.0(0.47) | 136 ± 4 | (10) | P <.001 |
| Levonantradol | 0.32(0.15) | 127 ± 4 | (10) | P <.001 |
| Levonantradol | 0.1(0.05) | 114 ± 5 | (5) | P = .1-.05 |

S.E. = standard error
P = probability - A value of 0.05 or less indicates statistically significant enhancement of binding. Determined by the two sample "t" test (one-sided) as described by Dixon & Massey in "Introduction to Statistical Analysis", McGraw-Hill, New York, 1969, pp. 114–119.

TABLE 6

Effect on $^3$H-flunitrazepam binding to mouse brain in vivo by (+)-nantradol

| Treatment | Dose s.c. μmoles/kg (mg/kg) | $^3$H-flunitrazepam binding % Control ± S.E. | No. of mice | Comparison with control |
|---|---|---|---|---|
| Control (vehicle) | — | 100 ± 2 | (10) | |
| (+)-Nantradol | 32(15) | 99 ± 6 | (10) | P >.05 |
| (+)-Nantradol | 10(4.7) | 94 ± 4 | (10) | P >.05 |
| (+)-Nantradol | 3.2(1.5) | 97 ± 5 | (10) | P >.05 |

Potentiation of Diazepam Antagonism of Pentylenetetrazol-Induced Clonic Convulsions in Mice by Levonantradol Groups of 10 mice were first treated subcutaneously with levonantradol or vehicle (ethanol-Emulphor EL-620-saline/5:5:90), with individual mice in each group receiving treatments at 10 minute intervals. At 1.0 or 1.25 hour after these pretreatments, individual mice received pentylenetetrazol, with the first mouse normally receiving 42.2 mg/kg i.p. The dose of pentylenetetrazol administered to the second mouse in the same drug group (10 minutes later) depended on the response of the first mouse: If he exhibited a clonic convulsion, then the second mouse received 32 mg/kg i.p. (−0.125 log dosage units); if the first mouse failed to convulse, the second mouse received 56.2 mg/kg i.p. (+0.125 log dosage units). This "up-and-down" procedure, with a continuum of pentylenetetrazol doses separated by 0.125 log dosage units, continued in the 10 mice, enabling efficient calculations of the logarithmic average threshold dose of pentylenetetrazol according to the method of Dixon and Massey (Introduction to Statistical Analysis, McGraw-Hill, New York, 1969, pp. 380–441). For some pretreatments, higher initial doses of pentylenetetrazol were used, but this did not invalidate comparative data, since pentylenetetrazol thresholds were calculated only from those doses received after the first dosage "reversal" had to be employed.

Levonantradol at 0.32 mg/kg s.c., a pharmacological dose, and one at least 10 times less than a dose that has no elevating effect on pentylenetetrazol threshold, was found to markedly potentiate the antipentylenetetrazol effect of diazepam. In Table 7 the third column from the left shows the dose-responsive increase in pentylenetetrazol threshold obtained with increasing doses of diazepam. Levonantradol (0.32 mg/kg s.c.) caused a striking increase in the pentylenetetrazol threshold of diazepam-treated mice (fourth column in Table 7).

This in vivo potentiation of a diazepam anticonvulsant effect is predicted by the in vitro and in vivo data described above showing that levonantradol facilitates binding of diazepam and flunitrazepam to benzodiazepine receptors. This finding provides in vivo evidence that levonantradol may have unexpected utility in potentiating the effects of diazepam in man. While the data were collected for an anticonvulsant endpoint in animals recognized to be uniquely responsive to diazepam-like benzodiazepines, the effect of levonantradol in enhancing the action of diazepam and other benzodiazepines may extend to anxiolytic, muscle relaxant and sedative uses of diazepam, in addition to its anticonvulsant uses.

TABLE 7

Potentiation of diazepam anticonvulsant activity by levonantradol; marked increase in pentylenetetrazol threshold of diazepam-treated mice by levonantradol

| | Threshold of Pentylenetetrazol for Producing Clonic Convulsions in Mice (mg/kg s.c.) | | |
|---|---|---|---|
| Dose (mg/kg s.c.) | Levonantradol Pretreatment | Diazepam Pretreatment | Levonantradol (0.32 mg/kg s.c.) + Diazepam Pretreatment |
| 0 | | 39–75* | 61 |
| 0.1 | | 65 | 87 |
| 0.32 | 61 | 77 | 133 |
| 1.0 | | 109 | 154 |
| 3.2 | 37 | 147 | 365 |
| 10 | | 173 | |
| 32 | | 244 | 301 |
| 100 | | 245 | |

*Range of pentylenetetrazol thresholds for control mice from ten experiments: 39, 39, 41, 49, 50, 56, 59, 62, 65, and 75 mg/kg s.c.

I claim:

1. A method of enhancing the binding of a benzodiazepine to central benzodiazepine receptors in a mammal which comprises concurrently administering to said mammal a benzodiazepine and a benzodiazepine enhancing amount of an analgesic agent having the formula

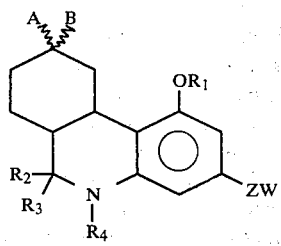

wherein
A and B when taken together are oxo;
A when taken individually is hydrogen;
B when taken individually is hydroxy or $(C_{2-5})$alkanoyloxy;
$R_1$ is hydrogen or $(C_{2-5})$alkanoyl;
$R_2$ is hydrogen or $(C_{1-6})$alkyl;
$R_3$ is hydrogen, methyl or ethyl;
$R_4$ is hydrogen or $(C_{1-6})$alkyl;
Z is alkylene having from one to nine carbon atoms or $(alk_1)_m$—O—$(alk_2)_n$ wherein each of $(alk_1)$ and $(alk_2)$ is alkylene having from one to nine carbon atoms, with the proviso that the summation of carbon atoms in $(alk_1)$ plus $(alk_2)$ is not greater than nine;
each of m and n is 0 or 1; and
W is hydrogen or

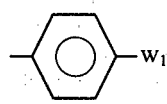

wherein $W_1$ is hydrogen, fluoro or chloro, or a pharmaceutically acceptable acid addition salt thereof, wherein said benzodiazepine is 7-chloro-2-methylamino-5-phenyl-3H-1,4-benzodiazepine-4-oxide; 8-chloro-6-phenyl-4H-[1,2,4]-triazolo[4,3-a][1,4]-benzodiazepine; 7-chloro-1,3-dihydro-3-hydroxy-5-phenyl-2H-1,4-benzodiazepin-2-one; 8-chloro-6-(2-chlorophenyl)-4H-[1,2,4]-(3-chlorotriazolo)[4,3-a]-[1,4]-benzodiazepine; 7-chloro-1,3-dihydro-1-methyl-5-phenyl-2H-1,4-benzodiazepine; 7-chloro-1,3-dihydro-1-methyl-5-(cyclohex-1-enyl)-2H-1,4-benzodiazepin-2-one; or those having formula II:

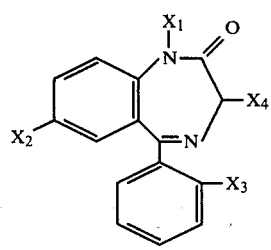

wherein the variables have the following values:

| | $X_1$ | $X_2$ | $X_3$ | $X_4$ |
|---|---|---|---|---|
| (a) | $CH_3$ | Cl | H | H |
| (b) | H | Cl | H | OH |
| (c) | H | Cl | H | H |
| (d) | $CH_3$ | $NO_2$ | F | H |
| (e) | $CH_2CH\equiv CH$ | Cl | H | H |

-continued

| | $X_1$ | $X_2$ | $X_3$ | $X_4$ |
|---|---|---|---|---|
| (f) | $CH_3$ | $NO_2$ | H | H |
| (g) | $CH_2CH_2N(C_2H_5)_2$ | Cl | F | H |
| (h) | H | Cl | H | COOK . KOH |
| (i) | H | $NO_2$ | Cl | H |
| (j) | H | Cl | Cl | OH |
| (k) | | Cl | H | H |
| | $CH_2$—◁ | | | |
| (l) | H | $NO_2$ | H | H |
| (m) | $CH_3$ | Cl | H | OH |
| (n) | $CH_3$ | Cl | H | $OCON(CH_3)_2$ | or a pharmaceutically acceptable salt of said benzodiazepine wherein the weight ratios of analgesic to benzodiazepine are from 1:1 to 1:00.

2. A method according to claim 1 wherein the benzodiazepine is 7-chloro-2-methylamino-5-phenyl-3H-1,4-benzodiazepine-4-oxide or a compound of formula II.

3. A method according to claim 2 wherein the analgesic agent has the formula

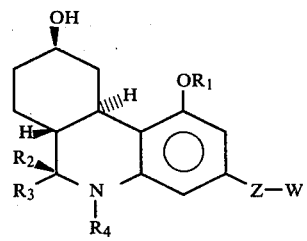

where $R_1$, $R_2$, $R_3$, $R_4$, Z and W are as defined in claim 1.

4. A method according to claim 3 wherein $R_1$ is hydrogen or acetyl; each of $R_2$, $R_3$ and $R_4$ is hydrogen or methyl; Z is —O—$(alk_2)$— and W is phenyl.

5. A method according to claim 4 wherein the benzodiazepine is

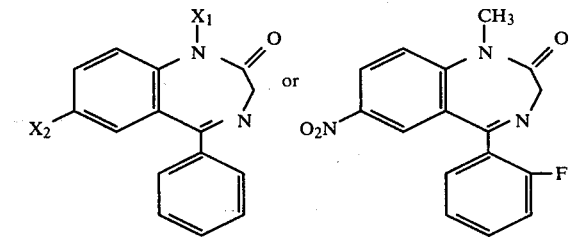

wherein $X_1$ is hydrogen or methyl and $X_2$ is chloro or nitro.

6. The method according to claim 5 wherein the benzodiazepine is

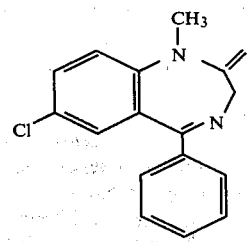

and the analgesic agent is

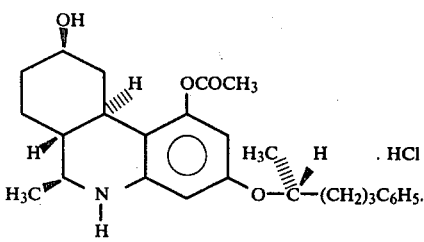

7. The method according to claim 5 wherein the benzodiazepine is

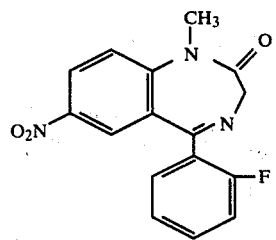

and the analgesic agent is

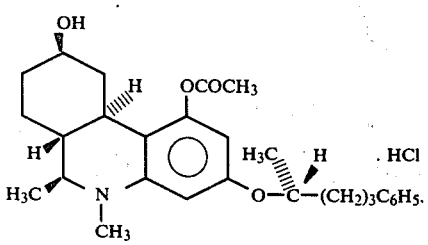

8. A pharmaceutical composition comprising a benzodiazepine and a benzodiazepine enhancing amount of an analgesic agent having the formula

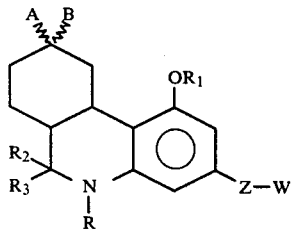

wherein
A and B when taken together are oxo;
A when taken individually is hydrogen;
B when taken individually is hydroxy or $(C_{2-5})$alkanoyloxy;
$R_1$ is hydrogen or $(C_{2-5})$alkanoyl;
$R_2$ is hydrogen or $(C_{1-6})$alkyl;
$R_3$ is hydrogen, methyl or ethyl;
$R_4$ is hydrogen or $(C_{1-6})$alkyl;
Z is alkylene having from one to nine carbon atoms or $(alk_1)_m$—O—$(alk_2)_n$ wherein each of $(alk_1)$ and $(alk_2)$ is alkylene having from one to nine carbon atoms, with the proviso that the summation of carbon atoms in $(alk_1)$ plus $(alk_2)$ is not greater than nine;

each of m and n is 0 or 1; and
W is hydrogen or

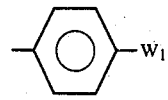

wherein $W_1$ is hydrogen, fluoro or chloro, or a pharmaceutically acceptable acid addition salt thereof, wherein said benzodiazepine is 7-chloro-2-methylamino-5-phenyl-3H-1,4-benzodiazepine-4-oxide; 8-chloro-6-phenyl-4H-[1,2,4]-triazolo[4,3-a][1,4]-benzodiazepine; 7-chloro-1,3-dihydro-3-hydroxy-5-phenyl-2H-1,4-benzodiazepin-2-one; 8-chloro-6-(2-chlorophenyl)-4H-[1,2,4]-(3-chlorotriazolo)[4,3-a]-[1,4]-benzodiazepine; 7-chloro-1,3-dihydro-1-methyl-5-phenyl-2H-1,4-benzodiazepine; 7-chloro-1,3-dihydro-1-methyl-5-(cyclohex-1-enyl)-2H-1,4-benzodiazepin-2-one; or those having formula II:

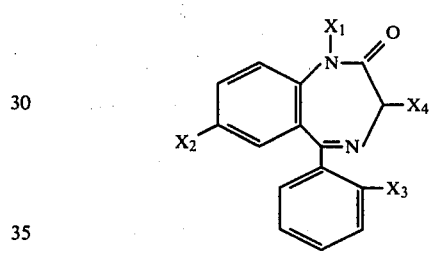

wherein the variables have the following values:

|     | $X_1$ | $X_2$ | $X_3$ | $X_4$ |
|-----|-------|-------|-------|-------|
| (a) | $CH_3$ | Cl | H | H |
| (b) | H | Cl | H | OH |
| (c) | H | Cl | H | H |
| (d) | $CH_3$ | $NO_2$ | F | H |
| (e) | $CH_2CH\equiv CH$ | Cl | H | H |
| (f) | $CH_3$ | $NO_2$ | H | H |
| (g) | $CH_2CH_2N(C_2H_5)_2$ | Cl | F | H |
| (h) | H | Cl | H | COOK . KOH |
| (i) | H | $NO_2$ | Cl | H |
| (j) | H | Cl | Cl | OH |
| (k) | $CH_2$—◁ | Cl | H | H |
| (l) | H | $NO_2$ | H | H |
| (m) | $CH_3$ | Cl | H | OH |
| (n) | $CH_3$ | Cl | H | $OCON(CH_3)_2$ | or a pharmaceutically acceptable salt of said benzodiazepine wherein the weight ratios of analgesic to benzodiazepine are from 1:1 to 1:00.

9. A composition according to claim 8 wherein the benzodiazepine is 7-chloro-2-methylamino-5-phenyl-3H-1,4-benzodiazepine-4-oxide or a compound of formula II.

10. A composition according to claim 9 wherein the analgesic agent has the formula

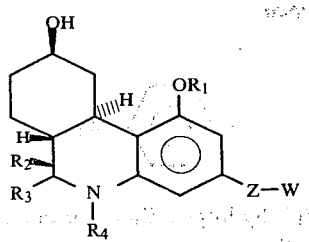

wherein R$_1$, R$_2$, R$_3$, R$_4$, Z and W are as defined in claim 3.

11. A composition according to claim 10 wherein R$_1$ is hydrogen or acetyl; each of R$_2$, R$_3$ and R$_4$ is hydrogen or methyl; Z is —O—(alk$_2$)— and W is phenyl.

12. A composition according to claim 11 wherein the benzodiazepine is

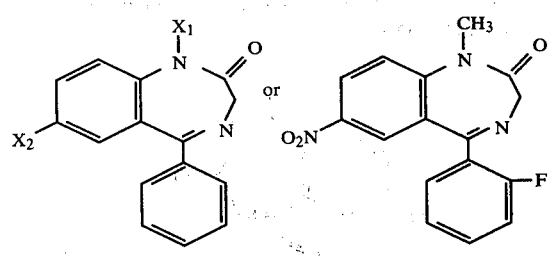

wherein X$_1$ is hydrogen or methyl and X$_2$ is chloro or nitro.

13. A composition according to claim 12 wherein the benzodiazepine is

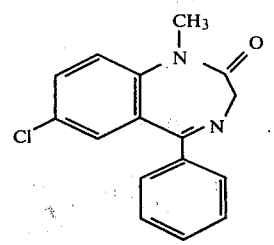

14. The composition according to claim 13 wherein the analgesic agent is

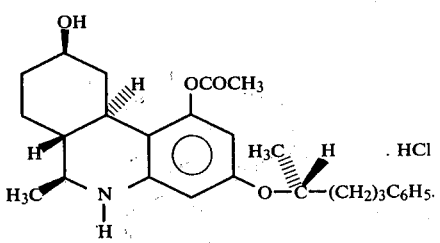

15. The composition according to claim 13 wherein the analgesic agent is

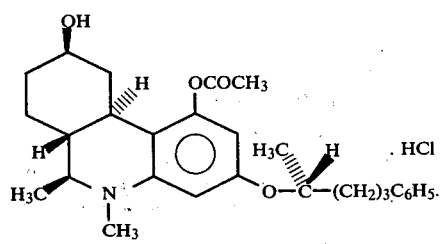

* * * * *